(12) United States Patent
Kobayashi

(10) Patent No.: US 8,491,465 B2
(45) Date of Patent: Jul. 23, 2013

(54) GUIDE TUBE, GUIDE TUBE APPARATUS, ENDOSCOPE SYSTEM, AND METHOD FOR SELF-PROPELLING GUIDE TUBE

(75) Inventor: Eiichi Kobayashi, Tama (JP)

(73) Assignee: Olympus Corporation (JP)

( * ) Notice: Subject to any disclaimer, the term of this patent is extended or adjusted under 35 U.S.C. 154(b) by 798 days.

(21) Appl. No.: 12/637,894

(22) Filed: Dec. 15, 2009

(65) Prior Publication Data

US 2010/0152537 A1 Jun. 17, 2010

(30) Foreign Application Priority Data

Dec. 17, 2008 (JP) ................................ 2008-321480

(51) Int. Cl.
*A61B 1/00* (2006.01)
(52) U.S. Cl.
USPC ........................................................ 600/114
(58) Field of Classification Search
USPC ...... 600/114; 396/17, 19; 346/107.2; 348/65, 348/82, 84–85
See application file for complete search history.

(56) References Cited

U.S. PATENT DOCUMENTS

| | | | | |
|---|---|---|---|---|
| 7,947,000 B2 * | 5/2011 | Vargas et al. | ................. | 600/587 |
| 7,998,060 B2 * | 8/2011 | Ferren et al. | ................. | 600/114 |
| 8,092,549 B2 * | 1/2012 | Hillis et al. | ................. | 623/23.64 |
| 2004/0008853 A1 * | 1/2004 | Pelrine et al. | ................. | 381/191 |
| 2007/0015966 A1 * | 1/2007 | Niwa et al. | ..................... | 600/114 |
| 2007/0221233 A1 * | 9/2007 | Kawano et al. | ................. | 128/899 |
| 2009/0012359 A1 * | 1/2009 | Tanaka et al. | ................. | 600/114 |

FOREIGN PATENT DOCUMENTS

| | | |
|---|---|---|
| JP | 63-49123 | 3/1988 |
| JP | 05-337081 | 12/1993 |
| JP | 09-201326 | 8/1997 |
| JP | 2004-041572 | 2/2004 |
| JP | 2005-261857 | 9/2005 |
| JP | 2009-066167 | 4/2009 |

OTHER PUBLICATIONS

Kazuya Isaki et al., Development of an Active Flexible Cable by Ciliary Vibration Drive for Scope Camera, Oct. 2006, Proceedings of the 2006 IEEE/RSJ International Conference on Intelligent Robots and Systems, pp. 3946-3951.*

Kazuya Isaki et al., "Development of an Active Flexible Cable Driven by Ciliary Vibration Mechanism," The 11th Robotics Symposia, pp. 414-419, Mar. 16, 2006.

Office Action issued by the Japanese Patent Office on Dec. 18, 2012 in connection with corresponding Japanese Patent Application No. 2008-321480.

* cited by examiner

*Primary Examiner* — Christopher Mahoney
(74) *Attorney, Agent, or Firm* — Ostrolenk Faber LLP

(57) ABSTRACT

A guide tube includes a tube; a ciliary portion composed of many cilia inclined in a longitudinal direction of the tube, provided in an outer peripheral portion of the tube; and a bag as a press mechanism for pressing an insertion portion of an endoscope inserted inside the tube.

6 Claims, 16 Drawing Sheets

GUIDE TUBE, GUIDE TUBE APPARATUS, ENDOSCOPE SYSTEM, AND METHOD FOR SELF-PROPELLING GUIDE TUBE

CROSS REFERENCE TO RELATED APPLICATION

This application claims benefit of Japanese Application No. 2008-321480 filed in Japan on Dec. 17, 2008, the contents of which are incorporated by this reference.

BACKGROUND OF THE INVENTION

1. Field of the Invention

The present invention relates to a guide tube, a guide tube apparatus, an endoscope system, and a method for self-propelling a guide tube.

2. Description of the Related Art

An endoscope apparatus is widely used for a purpose of observing a target in an interior connected to an exterior via a narrow space, which a user cannot directly view with his (her) eyes, and the like. The endoscope apparatus has an elongated insertion portion, and an image pickup portion, such as a CCD, is disposed at a distal end portion of the insertion portion. The user inserts the insertion portion to a target position and observes a target with a field of view of the CCD from the distal end portion.

An endoscope is used not only in a medical field, but also in an industrial field. Further, recently, the endoscope has also been used at a rescue site, such as a disaster site, for rescue of victims and the like.

It may not be easy for the user to insert a distal end portion of an elongated insertion portion of an endoscope to a target position in an interior via a narrow space. This is because it may be difficult to insert the insertion portion due to contact resistance between the insertion portion and a surrounding wall and the like.

Then, a so-called self-propelled endoscope apparatus is proposed in which when an insertion portion of an endoscope having a ciliary tape wound around an outer peripheral portion of the insertion portion is vibrated by a vibration motor, the insertion portion advances in a longitudinal direction of the insertion portion due to a frictional force between the insertion portion and surroundings. For example, a document, Kazuya Isaki et al., "Development of Active Cord-Like Body Driven by Ciliary Movement Mechanism," Proceedings of the 11th Robotics Symposia, Japan, Mar. 16, 2006, p. 414 to p. 419, discloses proposition of a self-propelled endoscope apparatus.

SUMMARY OF THE INVENTION

A guide tube according to the present embodiment includes a tube; a ciliary portion composed of many cilia inclined in a longitudinal direction of the tube, provided in an outer peripheral portion of the tube; and a press mechanism for pressing a member inserted inside the tube.

DETAILED DESCRIPTION OF THE PREFERRED EMBODIMENTS

First Embodiment

An endoscope system 1 in a first embodiment of the present invention, a guide tube 10 in the first embodiment, and a guide tube apparatus 20 in the first embodiment will be described below with reference to the drawings. Hereinafter, an endoscope system, a guide tube, and a guide tube apparatus are referred to as an endoscope system and the like.

Figure 1:
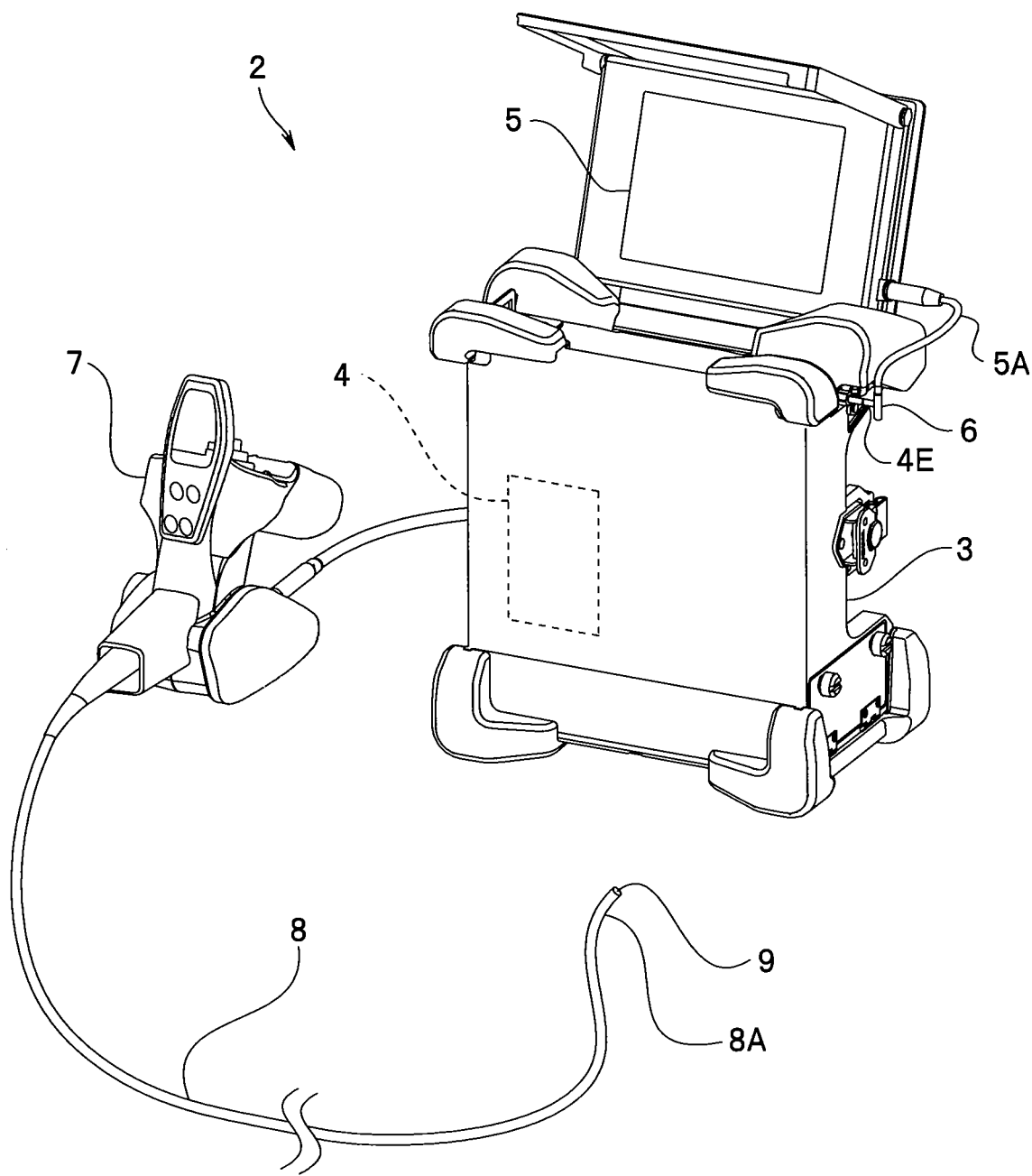
FIG. 1 is an appearance view showing an appearance of an endoscope apparatus used in combination with a so-called self-propelled guide tube apparatus in a first embodiment.
Figure 2:
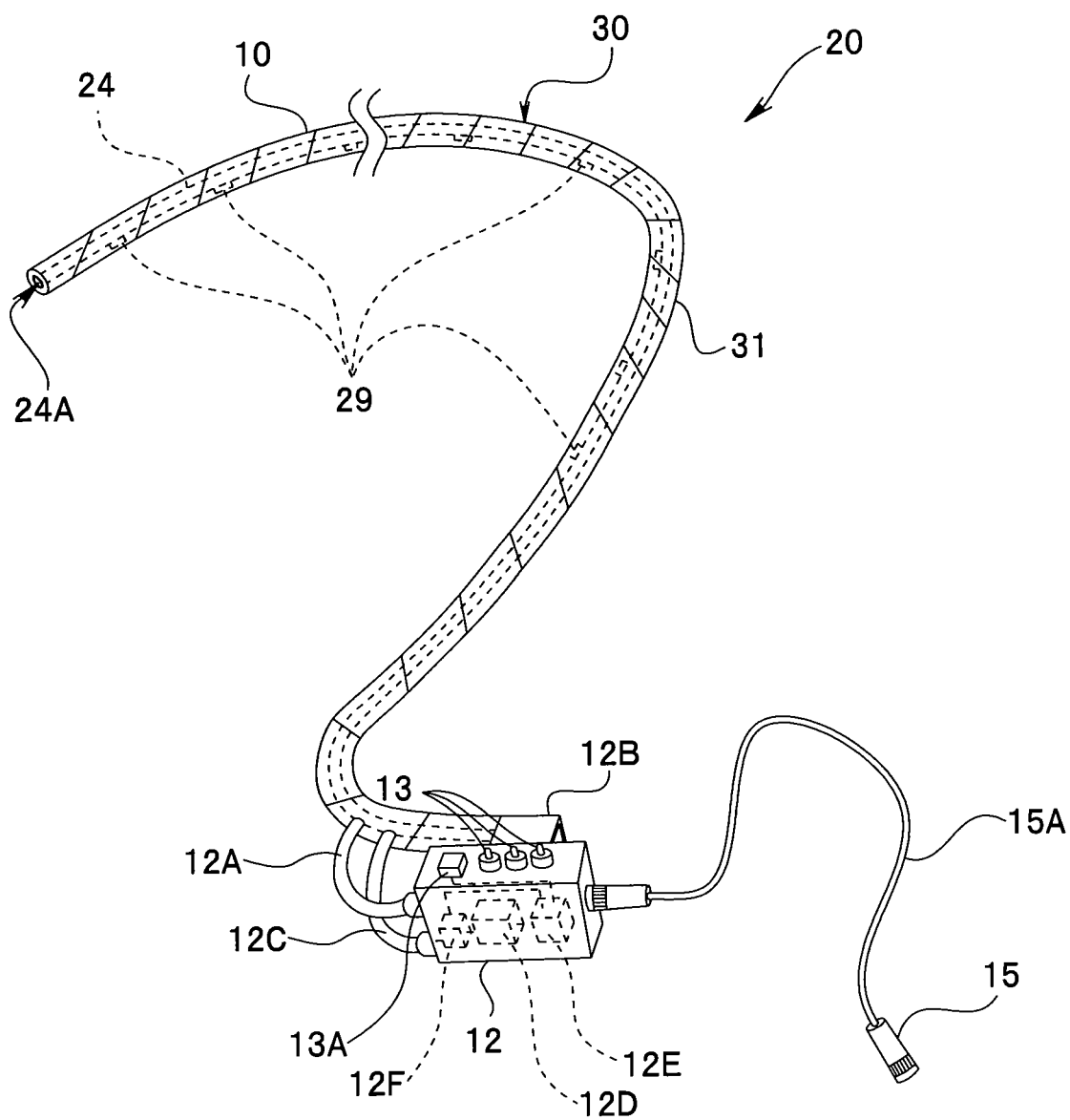
FIG. 2 is an appearance view showing an appearance of a guide tube apparatus in the first embodiment.
Figure 3:
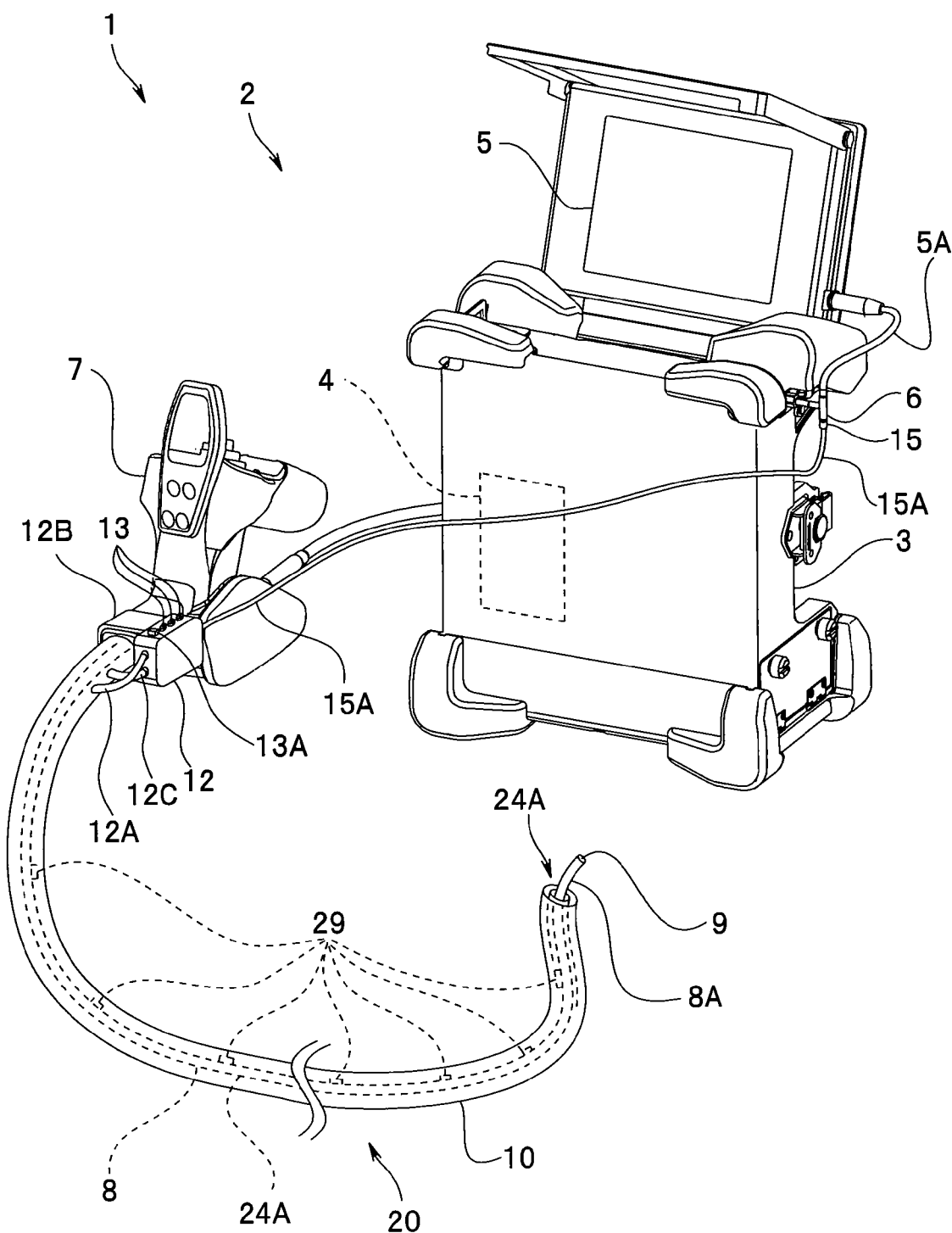
FIG. 3 is an appearance view showing an appearance of an endoscope system in the first embodiment.
Figure 4:
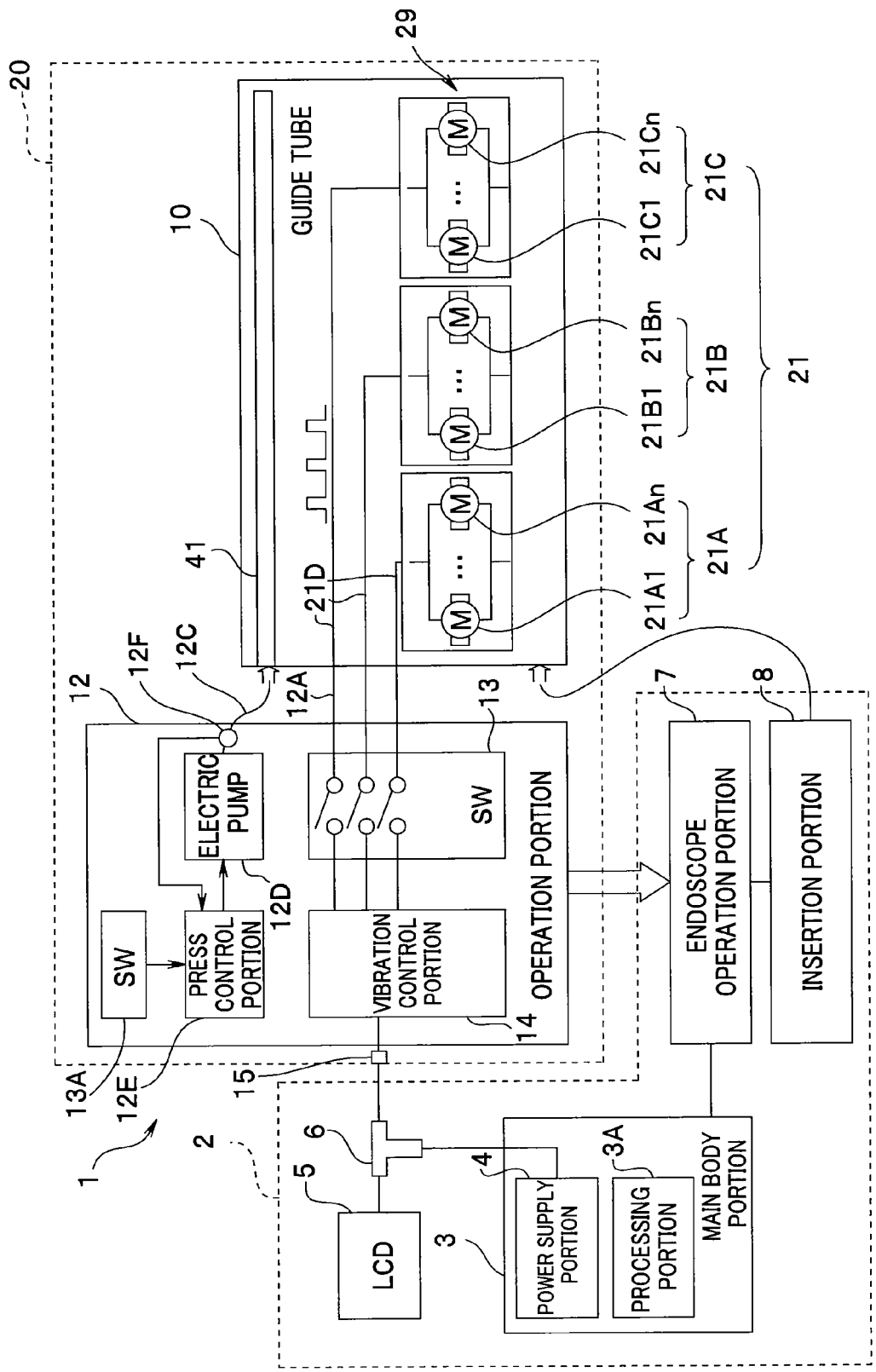
FIG. 4 is a configuration view showing a configuration of the endoscope system in the first embodiment.

FIG. 1 is an appearance view showing an appearance of an endoscope apparatus used in combination with a so-called self-propelled guide tube apparatus in the present embodiment. FIG. 2 is an appearance view showing an appearance of a guide tube apparatus in the present embodiment. FIG. 3 is an appearance view showing an appearance of an endoscope system in the present embodiment. FIG. 4 is a configuration view showing a configuration of the endoscope system in the present embodiment.

FIG. 1 shows an endoscope apparatus 2 used in combination with the guide tube apparatus 20 in the present embodiment. A basic configuration of the endoscope apparatus 2 is similar to that of a general-purpose endoscope apparatus, and the endoscope apparatus 2 has a main body portion 3, an endoscope operation portion 7, and an elongated insertion portion 8. A CCD 9, which is an image pickup portion, is disposed at a distal end portion 8A of the insertion portion 8. A power supply portion 4 for supplying power, and a processing portion 3A (see FIG. 4) composed of various processing boards and the like not shown are contained in the main body portion 3. An LCD 5, which is a display portion for displaying an endoscopic image and the like, is disposed detachably from the main body portion 3, and the LCD 5 operates by receiving supply of power from the power supply portion 4 in the main body portion 3. Further, the endoscope apparatus 2 has a connector 6, which is a power transmission connector, in order that the power supply portion 4 supplies power not only to the LCD 5 but also to the guide tube apparatus 20. The connector 6 has a structure for branching a power transmission line 4E from the power supply portion 4. In other words, the endoscope apparatus 2 is such that a power transmission connector for supplying power to an LCD in the general-purpose endoscope apparatus is replaced by the connector 6 having the branch structure, and a power transmission line 5A to the LCD 5 is connected to the connector 6.

On the other hand, the guide tube apparatus 20 shown in FIG. 2 has the guide tube 10 and a guide tube operation portion 12. The guide tube 10 has an elongated shape in which a tube 24 having an insertion hole 24A having an inner diameter such that the insertion portion 8 of the endoscope apparatus 2 can be inserted is a so-called core, and a ciliary portion 30 having many cilia 31 is provided in an outer peripheral portion of the tube 24. The ciliary portion 30 is provided by winding a ciliary tape around the tube 24. In the drawing, the cilia 31 themselves are not shown.

The cilia 31 of the ciliary tape, for example, have a diameter of 0.01 mm and a cilium length of 7 to 10 mm, are made of nylon, and are formed with a density of about 2500 cilia/cm$^2$. A ciliary tape having the cilia 31 inclined at a desired angle, for example, 60 degrees, can be obtained by subjecting a ciliary tape having the upright cilia 31, with the cilia inclined and deformed, to a heating process at a temperature equal to or higher than a thermoplastic deformation temperature of a material of the cilia 31 and a temperature decreasing process. The cilia 31 may be an inorganic substance, such as a metal wire and a metal plate, as long as the cilia 31 have a columnar structure.

By winding the ciliary tape having the inclined cilia 31 around the tube 24, the ciliary portion 30 having the cilia 31 inclined in a longitudinal direction of the tube 24 is formed. Here, the cilia 31 are preferably inclined in a proximal end portion direction to self-propel the guide tube 10 in a distal end direction. The cilia 31 of the ciliary tape inclined in the longitudinal direction have inclination at a spiral angle from the longitudinal direction of the tube 24 when the ciliary tape is spirally wound around the tube 24. In other words, an inclination direction of the cilia 31 need not perfectly match the longitudinal direction of the tube 24 and should have a longitudinal direction component. For example, the cilia 31 may be inclined at about 45 degrees from the longitudinal direction of the tube 24.

The guide tube operation portion 12 is connected via a power supply line 15A to a connector 15, which is a power receiving connector for receiving power, and drives vibration motors 21 in vibration portions 29 connected via a signal line 12A, by operation of a switch portion 13. A fixing jig 12B for attaching to and detaching from the endoscope operation portion 7 is disposed in the guide tube operation portion 12.

Further, a proximal end side of the guide tube 10 is fixed to the fixing jig 12B. When the fixing jig 12B is viewed from a user's hand side, the insertion hole 24A of the guide tube 10 is exposed so that the user can insert the insertion portion 8 of the endoscope.

Further, a duct 12C for supplying gas to a bag provided inside the guide tube 10, which is a tube, is provided between the guide tube operation portion 12 and the guide tube 10, as described later.

An electric pump 12D for supplying gas to the duct 12C, and a press control portion 12E for controlling operation of the electric pump 12D are included in the guide tube operation portion 12. An operation switch 13A for press control, together with the above-described switch portion 13, are provided in the guide tube operation portion 12. The switch 13A is connected to the press control portion 12E so that an operation signal of the switch 13A, which is a toggle switch or the like, is supplied to the press control portion 12E.

Also, a pressure sensor 12F for measuring pressure in the duct 12C is provided in the duct 12C, and an output of the pressure sensor 12F is supplied to the press control portion 12E.

Figure 5:
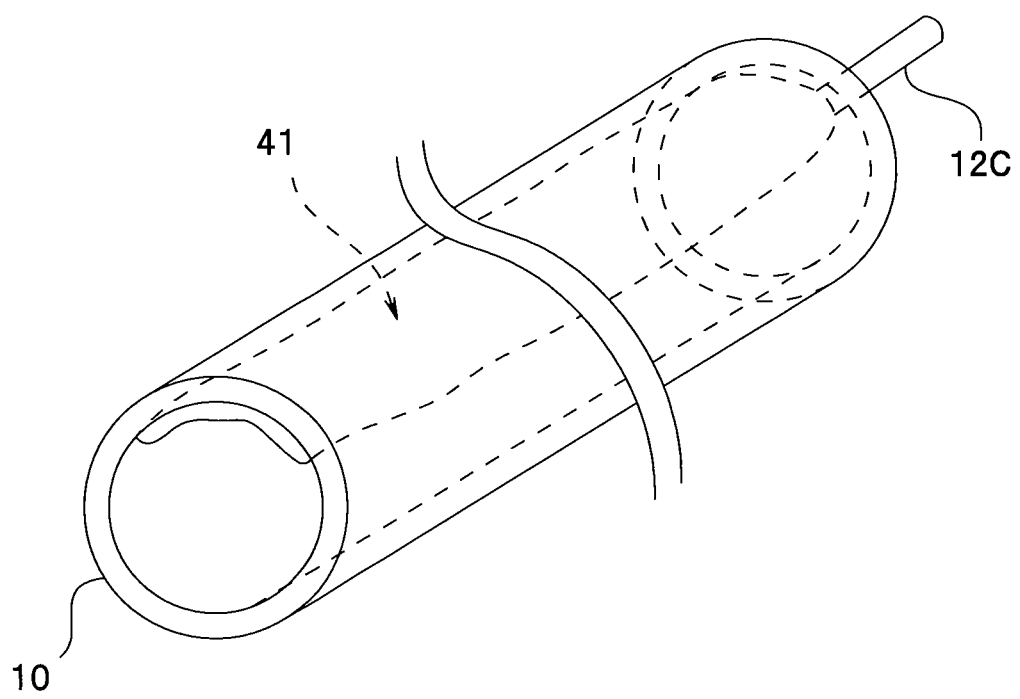
FIG. 5 is a view for explaining a bag provided inside a guide tube in the first embodiment.

FIG. 5 is a view for explaining the bag provided inside the guide tube 10. As shown in FIG. 5, a bag 41 is fixed inside the guide tube 10 by fixing means, such as an adhesive. The duct 12C for supplying gas from the electric pump 12D or sucking gas from an interior of the bag 41 is fixed at one end of the bag 41. One end of the duct 12C is connected to the bag 41, and the other end is connected to the electric pump 12D. The bag 41 is made of a fluororubber having good slidability, or a silicone rubber having a surface coated with fluorine.

As shown in FIG. 3, the endoscope system 1 is constituted by integrating the guide tube apparatus 20 and the endoscope apparatus 2. In other words, the insertion portion 8 of the endoscope apparatus 2 is inserted into the insertion hole 24A of the guide tube 10 from a fixing jig 12B side, and the guide tube operation portion 12 of the guide tube apparatus 20 is fixed to the endoscope operation portion 7 of the endoscope apparatus 2 by the fixing jig 12B. The connector 15, which is the power receiving connector of the guide tube apparatus 20, is connected to the connector 6, which is the power transmission connector of the endoscope apparatus 2. The power transmission connector may be disposed in the endoscope operation portion 7.

Next, as shown in FIG. 4, the guide tube operation portion 12 has a vibration control portion 14 for controlling vibration, and the switch portion 13 for selecting the vibration motors 21 that vibrate, and further has the press control portion 12E, the electric pump 12D, and the switch 13A, as described above. The guide tube apparatus 20 can drive only part of the vibration motors 21 selected by the switch portion 13, among the plurality of vibration motors 21 disposed at intervals in the longitudinal direction of the tube 24. In other words, the vibration motors 21 of the guide tube 10 illustrated in FIG. 4 are broadly divided into a vibration motor group 21A on a proximal end portion side, a vibration motor group 21B in a central portion, and a vibration motor group 21C on a distal end portion side, and can be driven for each vibration motor group. Each vibration motor group is composed of n (n≧an integer of 2) vibration motors, for example, 21A1 to 21An. Therefore, in the endoscope system 1 and the like, the user can selectively vibrate part of the guide tube 10.

The vibration control portion 14 and the press control portion 12E may be constituted by one control portion having both functions.

The endoscope system 1 is configured so that an outer diameter of the insertion portion 8 of the endoscope is smaller than an inner diameter of the insertion hole 24A of the guide tube 10, thereby, the insertion portion 8 can be inserted into the insertion hole 24A of the guide tube 10. However, when the guide tube 10 is vibrated, with the insertion portion 8 inserted, to self-propel the guide tube 10, the insertion portion 8 comes into contact with an inner wall of the insertion hole 24A, and so on, thereby, an exciting force on the cilia 31 is disturbed, and a desired self-propelling force may not be obtained.

Then, according to the present embodiment, the bag 41 that is expandable is provided in the guide tube 10, and when the guide tube 10 is vibrated to be self-propelled, the bag 41 is expanded to press the insertion portion 8. Thus, the insertion portion 8 does not come into contact with an inner wall of the guide tube 10 irregularly and continuously and so on during vibration of the guide tube 10. The bag 41 constitutes a press mechanism for pressing the insertion portion 8 of the endoscope inserted inside the tube 24.

Figure 6:
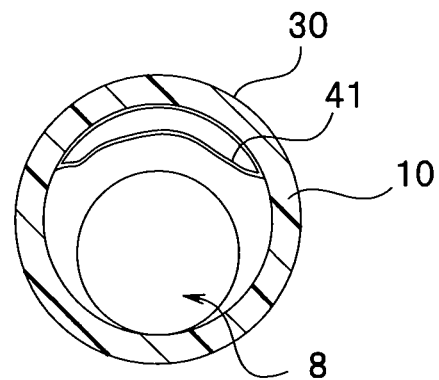
FIG. 6 is a cross-sectional view of the guide tube into which an insertion portion of an endoscope is inserted, showing a state in which the bag is not expanded in the guide tube in the first embodiment.

FIG. 6 is a cross-sectional view of the guide tube 10 into which the insertion portion 8 of the endoscope is inserted, showing a state in which the bag 41 is not expanded in the guide tube 10.

The bag 41 is provided on an inner peripheral surface of the tube 24 having the ciliary portion 30 in the outer peripheral portion. The bag 41 is fixed to the inner peripheral surface of the tube 24 along an axial direction of the tube 24 by an adhesive or the like, and has a space, into which gas can be introduced, in an interior.

In a state in which gas is not introduced into an interior of the bag 41, the insertion portion 8 is not fixed to an inner wall of the tube 24, so that the insertion portion 8 can be inserted into the tube 24, as shown in FIG. 6.

Figure 7:
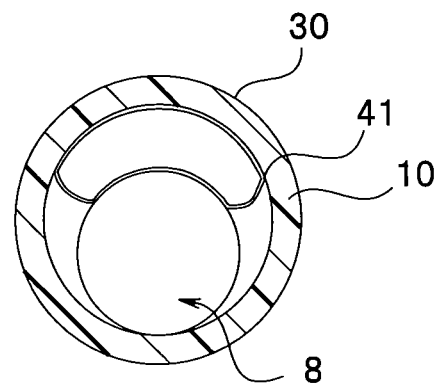
FIG. 7 is a cross-sectional view of the guide tube into which the insertion portion of the endoscope is inserted, showing a state in which the bag is expanded in the guide tube in the first embodiment.

FIG. 7 is a cross-sectional view of the guide tube 10 into which the insertion portion 8 of the endoscope is inserted, showing a state in which the bag 41 is expanded in the guide tube 10.

In a state in which gas is introduced into the interior of the bag 41 and the bag 41 is expanded, the insertion portion 8 is pressed and fixed to the inner wall of the tube 24 by the bag 41, as shown in FIG. 7.

Therefore, the insertion portion 8 of the endoscope is inserted into the guide tube 10 in the state in FIG. 6, and after insertion, gas is introduced into the interior of the bag 41 to expand the bag 41 to press and fix the insertion portion 8 to the inner wall of the guide tube 10. In the state in FIG. 7, the insertion portion 8 is fixed in an interior of the guide tube 10 when the guide tube 10 vibrates, and therefore, the insertion portion 8 does not come into contact and so on in the insertion hole 24A. Therefore, when the guide tube 10 is vibrated, an exciting force is sufficiently applied to the cilia 31, thereby, the guide tube 10 can be suitably self-propelled toward a target.

When the bag 41 is expanded, the user operates the electric pump 12D to supply gas, such as air, to the bag 41 via the duct 12C by turning the switch 13A to an on side. Pressure in the duct 12C is measured by the pressure sensor 12F, and therefore, when a predetermined pressure is reached, the press control portion 12E stops operation of the electric pump 12D.

Also, the user can operate the electric pump 12D to suck gas from the bag 41 by turning the switch 13A to an off side or a suction side. The press control portion 12E also determines stop of gas suction operation, based on a detected value of the pressure sensor 12F, and stops operation of the electric pump 12D.

As described above, according to the endoscope system in the present embodiment, a desired self-propelling force can be obtained when the guide tube is a self-propelled type, even in a state in which the insertion portion of the endoscope is inserted into the interior.

In the above-described example, gas is introduced into the bag constituting the press mechanism, but liquid may be introduced.

Further, when it is desired to perform observation using another type of endoscope after a guide tube is inserted to a target position at a disaster site and the like, gas in a bag in the guide tube is sucked as described above, and an endoscope insertion portion is pulled out, then, an insertion portion of another endoscope is inserted into the guide tube. The user can perform observation and the like with another endoscope, with such simple work.

Figure 8:
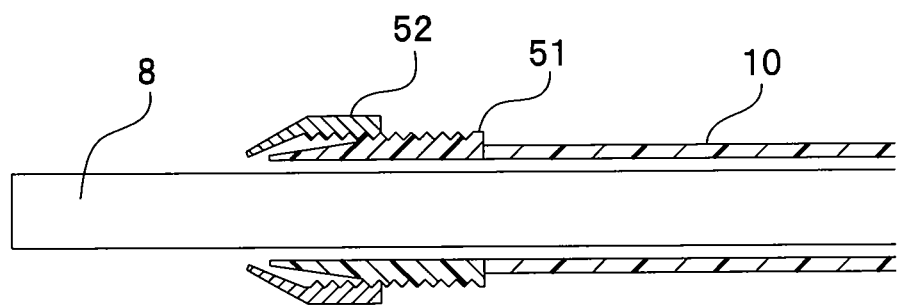
FIG. 8 is a cross-sectional view showing a state in which a tightening mechanism provided at a distal end portion of the guide tube does not tighten the insertion portion in the first embodiment.
Figure 9:
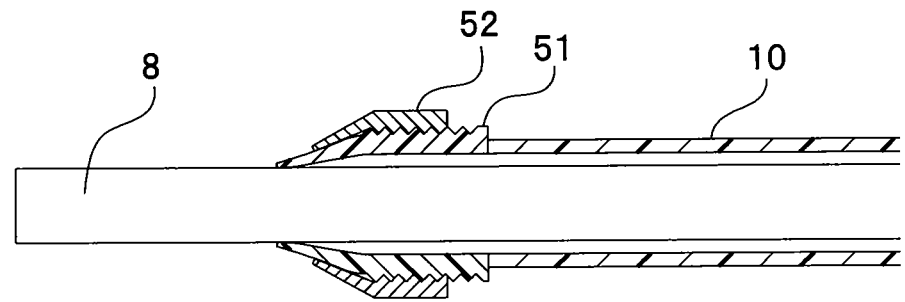
FIG. 9 is a cross-sectional view showing a state in which the tightening mechanism provided at the distal end portion of the guide tube tightens the insertion portion in the first embodiment.

Also, a tightening mechanism may be provided at a distal end portion of the guide tube 10 to fix the insertion portion 8 of the endoscope at the distal end portion of the guide tube 10. FIG. 8 and FIG. 9 are cross-sectional views for explaining an example of a tightening mechanism provided at the distal end portion of the guide tube 10.

FIG. 8 is a cross-sectional view showing a state in which the tightening mechanism provided at the distal end portion of the guide tube 10 does not tighten the insertion portion 8. FIG. 9 is a cross-sectional view showing a state in which the tightening mechanism provided at the distal end portion of the guide tube 10 tightens the insertion portion 8.

A cylinder 51 of resin or the like is attached at the distal end portion of the guide tube 10. The cylinder 51 has a cylindrical shape in which a thickness of a tube wall on a distal end side is thin, and has a plurality of cut portions (not shown), that is, a plurality of slits, on a circumferential surface of the cylinder 51 from the distal end side in a direction parallel to an axis of the cylinder 51. An outer peripheral portion of the generally cylindrical cylinder 51 on the distal end side has a conical shape in which the distal end side is cut off, and the outer peripheral portion from a proximal end side, on which the guide tube 10 is fixed, to a central portion is threaded.

A cylinder 52 that is threaded on an inner peripheral side to threadedly engage a screw thread formed on a surface of the cylinder 51 is provided on an outer peripheral side of the cylinder 51. An outer peripheral portion of the generally cylindrical cylinder 52 of resin or the like on a distal end side has a conical shape in which the distal end side is cut off. The distal end side of the cylinder 52 is configured so that an inner diameter becomes gradually smaller toward the distal end side. The cylinder 51 and the cylinder 52 have a so-called bolt and nut relationship. The cylinders 51 and 52 constitute a tightening mechanism.

FIG. 8 shows a state in which the tightening mechanism does not tighten the insertion portion 8, and a distal end portion of the cylinder 51 is not pressed in an inner diameter direction by a distal end portion of the cylinder 52. Therefore, the cylinder 52 does not press an outer peripheral portion of the insertion portion 8.

FIG. 9 shows a state in which the tightening mechanism tightens the insertion portion 8. The user rotates the cylinder 52, thereby, the distal end portion of the cylinder 51 is gradually pressed in the inner diameter direction by the distal end portion of the cylinder 52, and an inner peripheral portion of the cylinder 51 on the distal end side is pressed by the cylinder 52. As a result, the insertion portion 8 is fixed to the cylinder 51, that is, the guide tube 10.

Therefore, the user can also fix the insertion portion 8 at the distal end portion of the guide tube 10, using the tightening mechanism, after inserting the insertion portion 8 of the endoscope into the guide tube 10.

The tightening mechanism at the distal end portion of the guide tube described using FIG. 8 and FIG. 9 can also be similarly applied to other embodiments described below.

Second Embodiment

Figure 10:
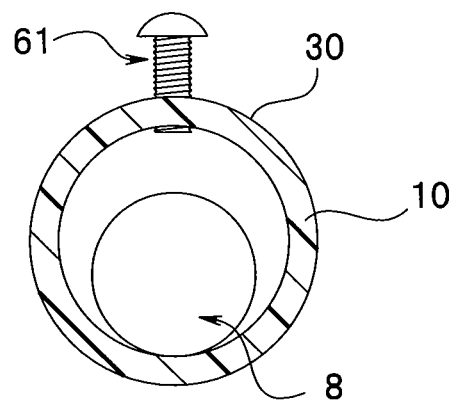
FIG. 10 is a cross-sectional view showing a state in which a screw does not press an insertion portion of an endoscope according to a second embodiment.
Figure 11:
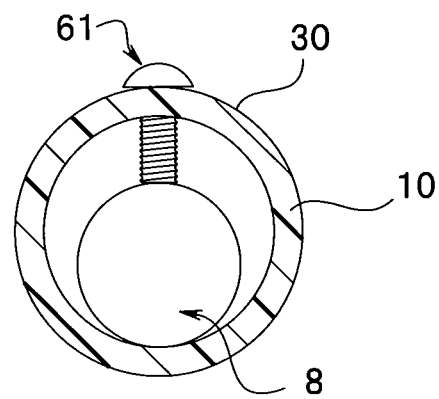
FIG. 11 is a cross-sectional view showing a state in which the screw presses the insertion portion of the endoscope according to the second embodiment.

FIG. 10 and FIG. 11 are cross-sectional views for explaining a press mechanism according to a second embodiment. FIG. 10 is a cross-sectional view showing a state in which a screw as a press mechanism for pressing and fixing the insertion portion 8 of the endoscope inserted into the guide tube 10 does not press the insertion portion of the endoscope. FIG. 11 is a cross-sectional view showing a state in which the screw presses the insertion portion of the endoscope. A screw 61 is provided to threadedly engage a screw hole (not shown) provided in a tube wall portion of the tube 24 of the guide tube 10, toward a direction orthogonal to the tube wall portion (that is, an axis of the tube 24).

The screw 61, which is a press member provided in the tube 24, is provided in a plurality of places at predetermined intervals along an axial direction of the guide tube 10. The screw hole is preferably provided in the distal end portion of the guide tube 10, and portions where the vibration motor is located. After inserting the insertion portion 8 into the insertion hole 24A of the guide tube 10, the user rotates each screw 61 until a distal end portion of the screw 61 inside the tube 24 hits and presses the insertion portion 8. The distal end portion of the screw 61, which is a press member, presses the outer peripheral portion of the insertion portion 8 of the endoscope with sufficient force, thereby, the insertion portion 8 can be fixed to the guide tube 10.

The press member in the present embodiment is the screw 61 provided in the tube 24, and the user can perform fixing work only with a driver. Therefore, fixing of the insertion portion 8 to the guide tube 10 can be easily performed.

Figure 12:
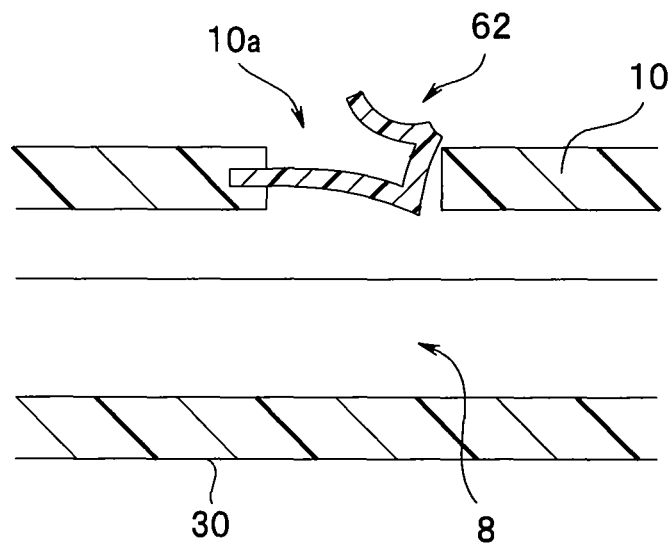
FIG. 12 is a cross-sectional view showing a state in which a spring member does not press the insertion portion of the endoscope according to the second embodiment.
Figure 13:
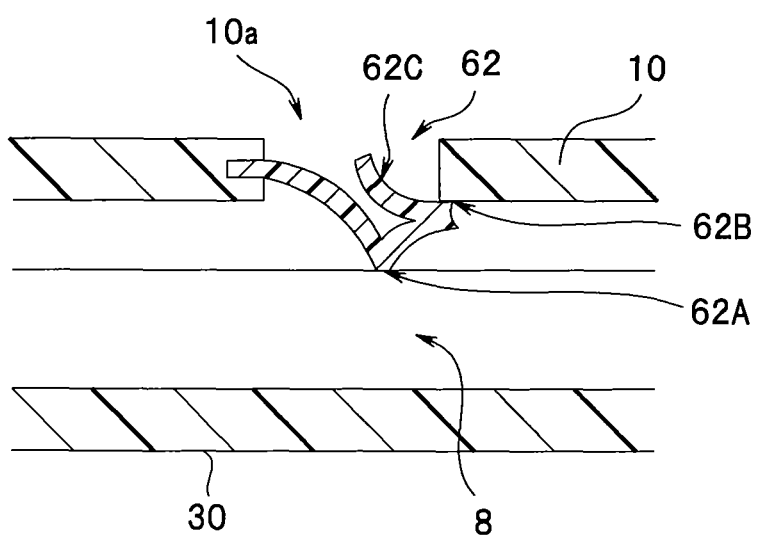
FIG. 13 is a cross-sectional view showing a state in which the spring member presses the insertion portion of the endoscope according to the second embodiment.

In the above example, a spring member may be used as a press member, instead of the screw 61. FIG. 12 and FIG. 13 show an example in which the press member is a spring member. FIG. 12 is a cross-sectional view showing a state in which the spring member does not press the insertion portion of the endoscope. As a press member, one end of a spring member 62 is fixed to a tube wall portion of an opening portion 10a provided in the tube 24, and the other end is a movable end.

The spring member is a plate-like spring member whose cross-sectional shape is a squared U-shape, and is made of an elastically deformable member, for example, a resin member or a metal member. A plurality of the spring members 62 as shown in FIG. 12 are provided in a plurality of the opening portions 10a provided in the tube 24. The opening portion 10a is preferably provided in the distal end portion of the guide tube 10, and the portions where the vibration motor is located.

FIG. 13 is a cross-sectional view showing a state in which the spring member presses the insertion portion of the endoscope. The user presses a free end portion 62C of the spring member 62 into an interior of the tube 24 with his (her) fingers or the like, thereby, a part 62A of a central portion of the spring member 62 presses the outer peripheral portion of the insertion portion 8 in the interior of the tube 24, and another part is engaged with an inner peripheral portion of the tube 24. As a result, the insertion portion 8 can be fixed to the guide tube 10. When a fixed state is released, the user pulls out the free end portion 62C outside with his (her) fingers or the like, thereby, the spring member 62 can be deformed and returned to the state in FIG. 12.

The press member in the present embodiment is the spring member provided in the tube 24, and the user can perform fixing work only by pressing one end of the spring member. Therefore, fixing of the insertion portion 8 to the guide tube 10 can be easily performed.

Figure 14:
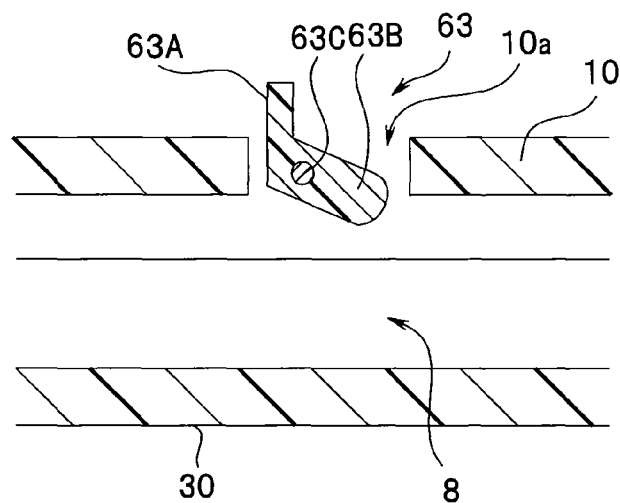
FIG. 14 is a cross-sectional view showing a state in which a rotating member does not press the insertion portion of the endoscope according to the second embodiment.
Figure 15:
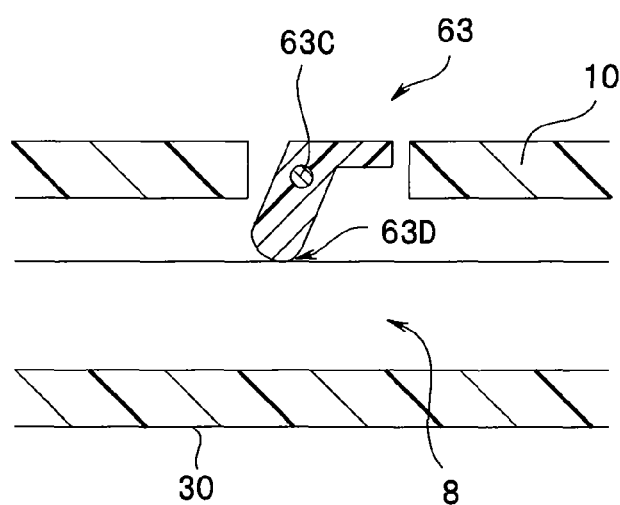
FIG. 15 is a cross-sectional view showing a state in which the rotating member presses the insertion portion of the endoscope according to the second embodiment.
Figure 16:
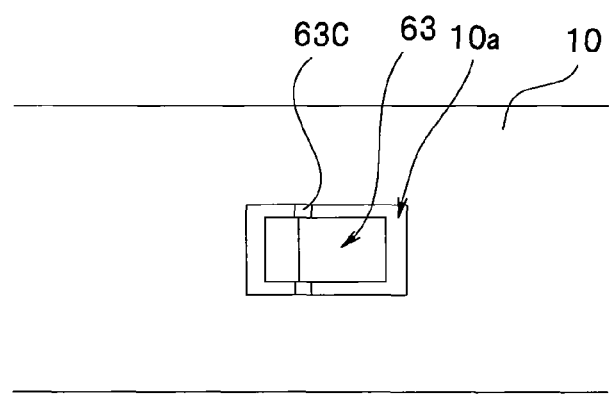
FIG. 16 is a plan view of a guide tube including the rotating member according to the second embodiment.

Further, a rotating member may be used as another example of the press member. FIG. 14 to FIG. 16 show an example in which the press member is a rotating member. FIG. 14 is a cross-sectional view showing a state in which the rotating member does not press the insertion portion of the endoscope. FIG. 15 is a cross-sectional view showing a state in which the rotating member presses the insertion portion of the endoscope. FIG. 16 is a plan view of a guide tube including the rotating member.

As a press member, a rotating member 63 is rotatably provided in the opening portion 10a provided in the tube 24. The rotating member 63 is a dog leg-shaped member of a hard resin or the like. One end side of the rotating member 63 is an operation piece portion 63A, and the other end has an action piece portion 63B. The rotating member 63 is adapted to be rotatable around an axis of a shaft member 63C provided in the opening portion 10a by passing the shaft member 63C through a center of the rotating member 63. A plurality of the rotating members 63 as shown in FIG. 14 are provided in the plurality of opening portions 10a provided in the tube 24. Also in this case, the opening portion 10a is preferably provided in the distal end portion of the guide tube 10, and the portions where the vibration motor is located.

When inserting the insertion portion 8 of the endoscope into the tube 24, the user puts the rotating member 63 in the state in FIG. 14. After finishing insertion of the insertion portion 8, the user brings down the operation piece portion 63A of the rotating member 63 on an opening portion 10a side with his (her) fingers or the like, thereby, the rotating member 63 rotates, and the action piece portion 63B presses and fixes the outer peripheral portion of the insertion portion 8. As a result, the insertion portion 8 can be fixed to the guide tube 10. When a fixed state is released, the user pulls out the operation piece portion 63A outside away from the opening portion 10a with his (her) fingers or the like, thereby, the rotating member 63 can be rotated and returned to the state in FIG. 14.

The press member in the present embodiment is the rotating member, and the user can perform fixing work only by rotating one end of the rotating member. Therefore, fixing of the insertion portion 8 to the guide tube 10 can be easily performed.

As described above, according to the present embodiment, the user can easily press and fix the insertion portion of the endoscope to the guide tube with the press member as the press mechanism.

Third Embodiment

Figure 17:
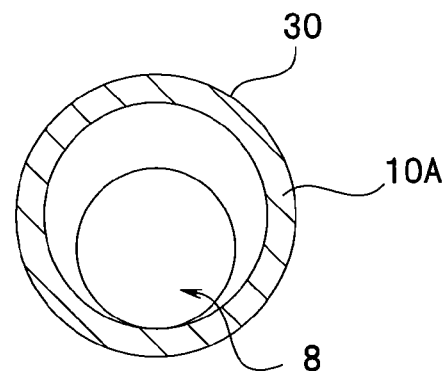
FIG. 17 is a cross-sectional view showing a state in which an inner wall portion of a physically plastically deformable tube as a press mechanism for pressing and fixing an insertion portion of an endoscope inserted into a guide tube does not press the insertion portion according to a third embodiment.
Figure 18:
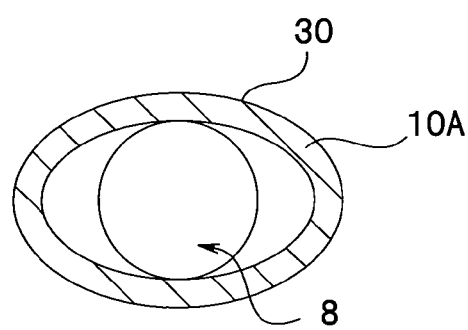
FIG. 18 is a cross-sectional view showing a state in which the inner wall portion of the physically plastically deformed tube presses the insertion portion according to the third embodiment.

FIG. 17 and FIG. 18 are cross-sectional views for explaining a press mechanism according to a third embodiment. FIG. 17 is a cross-sectional view showing a state in which an inner wall portion of a physically plastically deformable tube 24 as a press mechanism for pressing and fixing the insertion portion 8 of the endoscope inserted into a guide tube 10A does not press the insertion portion 8. FIG. 18 is a cross-sectional view showing a state in which the inner wall portion of the physically plastically deformed tube 24 presses the insertion portion 8. The guide tube 10A is a tube body of a material whose shape is plastically deformed by an external force on an outer peripheral portion. Examples of the plastically deformable material include aluminum, SUS (stainless steel), brass, and the like. Therefore, the guide tube 10A is formed as a tubular member by working a plate material of these materials.

The guide tube 10A is plastically deformed by being partly pressed from outside, and an inner peripheral surface of the guide tube 10A presses the outer peripheral portion of the insertion portion 8 of the endoscope, thereby, the insertion portion 8 is fixed to the guide tube 10A.

As a way of applying an external force to the guide tube 10A, the user may step on the guide tube 10A with his (her) foot, or strike the guide tube 10A with a hammer or the like.

Figure 19:
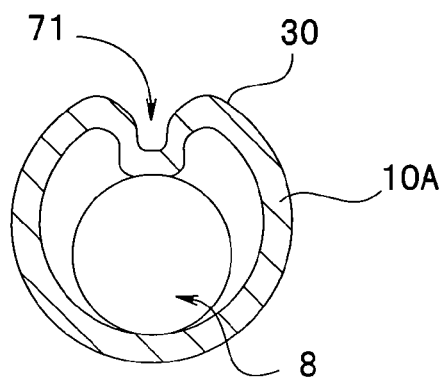
FIG. 19 is a cross-sectional view for explaining an example in which the guide tube is locally plastically deformed according to the third embodiment.

Further, the guide tube 10A may be locally plastically deformed using a tool, such as a punch. FIG. 19 is a cross-sectional view for explaining an example in which the guide tube is locally plastically deformed.

As shown in FIG. 19, by using a tool, such as a punch, the user can form a depression 71 in the outer peripheral portion of the guide tube 10A.

In FIG. 18 and FIG. 19, plastically deformed portions are preferably a distal end portion of the guide tube 10A, and portions where the vibration motor is located.

Also, the entire tube 24 may be plastically deformed, or the tube 24 may be partly plastically deformed in a plurality of places.

When the user forms portions pressed from outside, in a plurality of places in the outer peripheral portion of the guide tube 10A, using his (her) foot, a tool, or the like, the user can fix the insertion portion 8 to the guide tube 10A.

The tube itself may be entirely or partly formed of a shape memory alloy so that the tube can be plastically deformed using temperature.

Fourth Embodiment

In the third embodiment, the guide tube itself is a plastically deformable material. However, in the present embodiment, the guide tube itself is not physically plastically deformed, but the guide tube is deformed to shrink in an inner diameter direction to fix the insertion portion of the endoscope.

Figure 20:
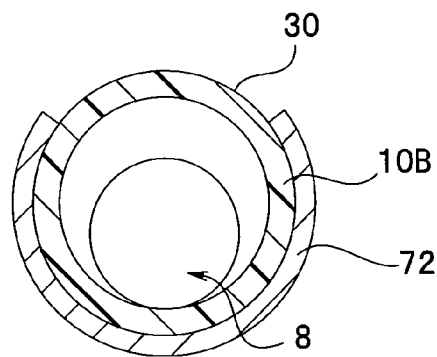
FIG. 20 is a cross-sectional view showing a state before a plastically deformable member is plastically deformed according to a fourth embodiment.
Figure 21:
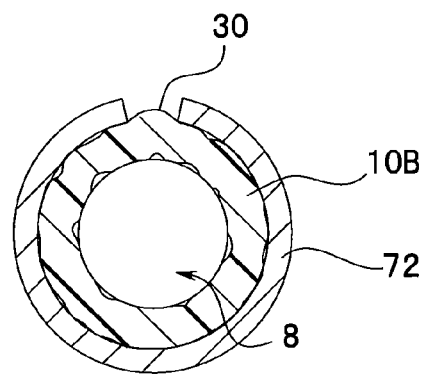
FIG. 21 is a cross-sectional view showing a state after the plastically deformable member is plastically deformed according to the fourth embodiment.
Figure 22:
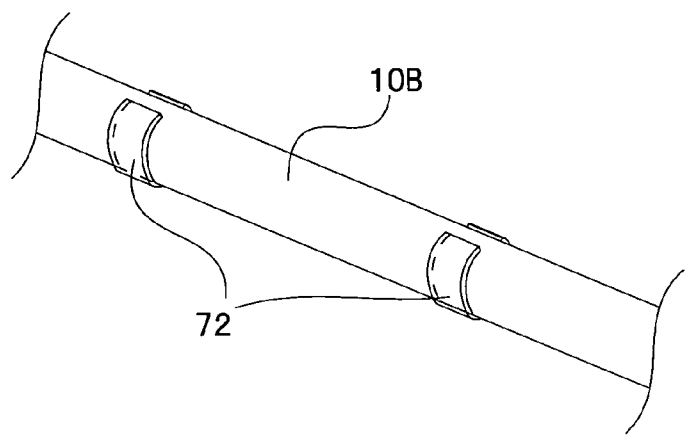
FIG. 22 is a partial appearance view showing a state in which a plurality of the plastically deformable members are provided around a guide tube according to the fourth embodiment.

FIG. 20 to FIG. 22 are views for explaining a first example in which a plurality of plastically deformable members are provided around a guide tube. FIG. 20 is a cross-sectional view showing a state before the plastically deformable member is plastically deformed. FIG. 21 is a cross-sectional view showing a state after the plastically deformable member is plastically deformed. FIG. 22 is a partial appearance view showing a state in which the plurality of plastically deformable members are provided around the guide tube.

As shown in FIG. 22, a C-shaped member 72 as a plastically deformable member is attached in a plurality of places on a guide tube 10B at predetermined intervals. The guide tube 10B is made of a polyester resin, a polyurethane resin, or the like. The C-shaped member 72 is a metal member attached to the guide tube 10B so as to surround a periphery of the guide tube 10B. The C-shaped member 72 is preferably provided in the distal end portion of the guide tube 10B, and portions where the vibration motor is located.

When the insertion portion 8 of the endoscope is inserted into a tube 24, the C-shaped members 72 are in the state in FIG. 20. When insertion of the insertion portion 8 is finished, an external force such that an inner diameter of the C-shaped members 72 decreases is applied by pincers or the like to put the C-shaped members 72 in the state in FIG. 21. In the state in FIG. 21, the C-shaped members 72 maintain a shape, and therefore, the guide tube 10B inside is shrunk from an outer peripheral portion by press of the C-shaped members 72. As a result, the insertion portion 8 is pressed by an inner peripheral surface of the guide tube 10B and fixed to the guide tube 10B.

As described above, by providing one or a plurality of the plastically deformable members, as shown in FIG. 20 to FIG. 22, around the guide tube and plastically deforming the member(s), the insertion portion of the endoscope can be fixed to the guide tube.

A shape memory alloy may be used for the C-shaped member 72 as a press mechanism to plastically deform the C-shaped member 72 using temperature.

Figure 23:
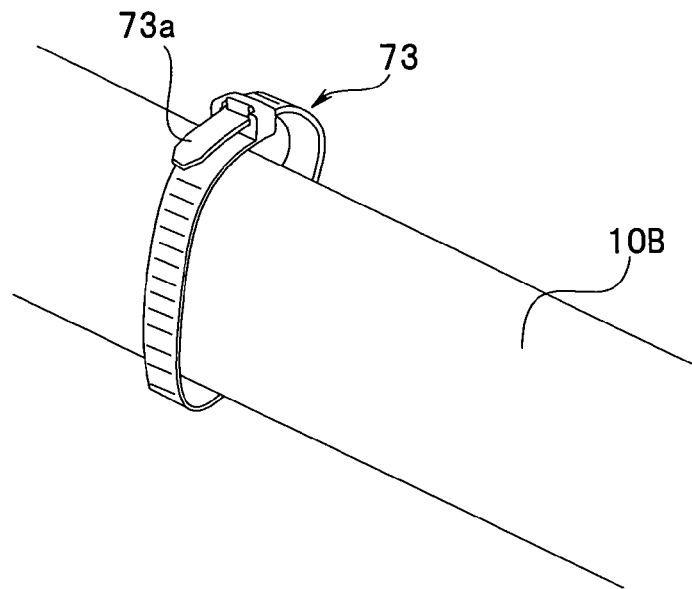
FIG. 23 is a partial appearance view for explaining a state when a binding band as a press mechanism is in a non-binding state according to the fourth embodiment.
Figure 24:
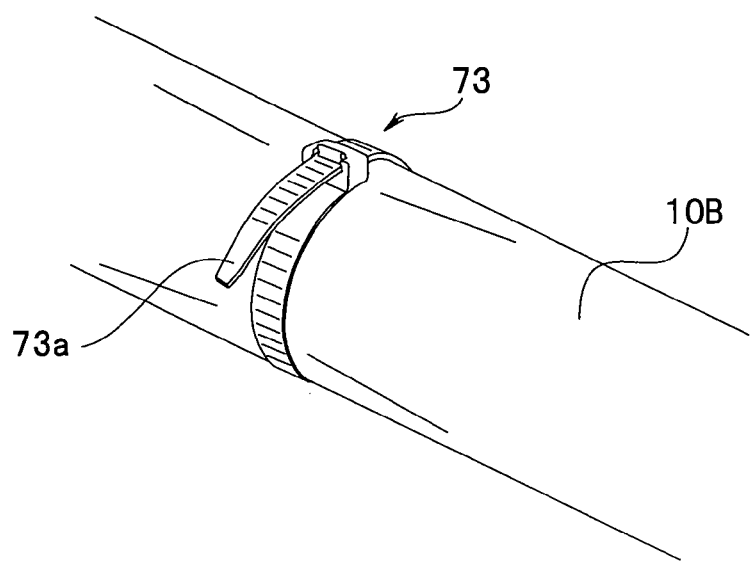
FIG. 24 is a partial appearance view for explaining a state when the binding band as the press mechanism is in a binding state according to the fourth embodiment.

FIG. 23 and FIG. 24 are views for explaining an example in which a tightening member, such as a cable tie, is provided around the guide tube.

FIG. 23 is a partial appearance view for explaining a state when a binding band 73 as a press mechanism is in a non-binding state. Part of the binding band 73 is wound around the guide tube 10B, and when the insertion portion 8 is inserted into the guide tube 10B, the binding band 73 shown in FIG. 23 is in a non-binding state. The binding band 73 is, for example, a string-like member made of an elastomer.

When insertion of the insertion portion 8 is finished, the binding band 73 is put in a binding state, in other words, a state in which the guide tube 10B is tightened, as shown in FIG. 24, to fix the insertion portion 8 to the guide tube 10B.

FIG. 24 is a partial appearance view for explaining a state when the binding band 73 as the press mechanism is in a binding state. By pulling a distal end portion 73a of the binding band 73, the guide tube 10B can be easily pressed from an outer peripheral side to fix the insertion portion 8 to the guide tube 10B. The binding band 73 is preferably provided in the distal end portion of the guide tube 10B, and the portions where the vibration motor is located.

Figure 25:
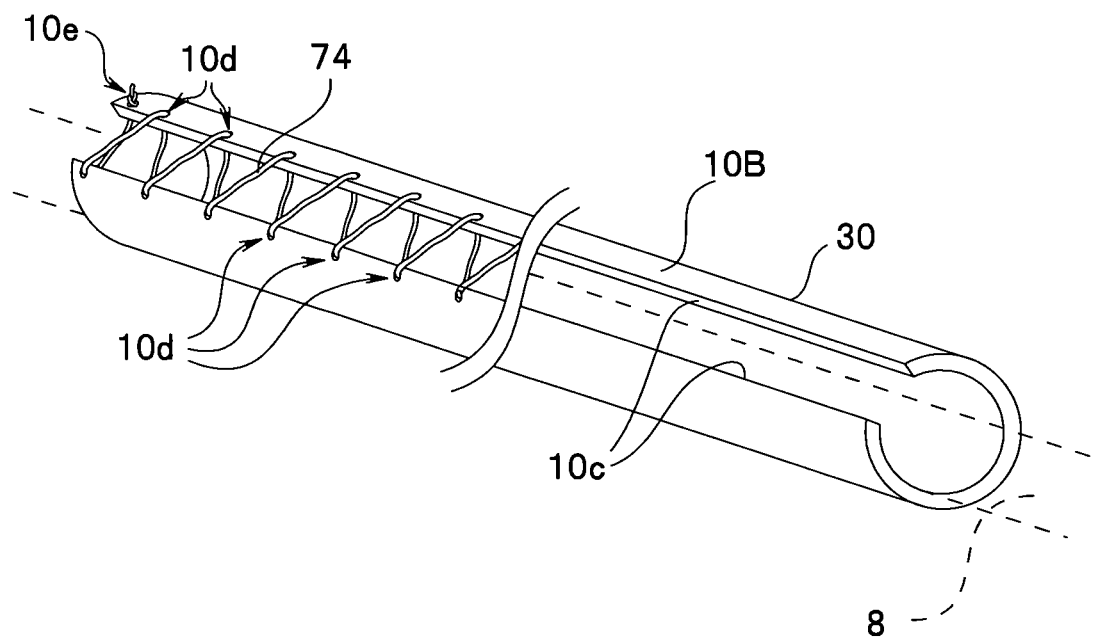
FIG. 25 is a view showing a state in which with a string-like member as a press mechanism for pressing and fixing an insertion portion of an endoscope inserted into a guide tube being loose, an inner peripheral surface of the guide tube does not press the insertion portion according to the fourth embodiment.
Figure 26:
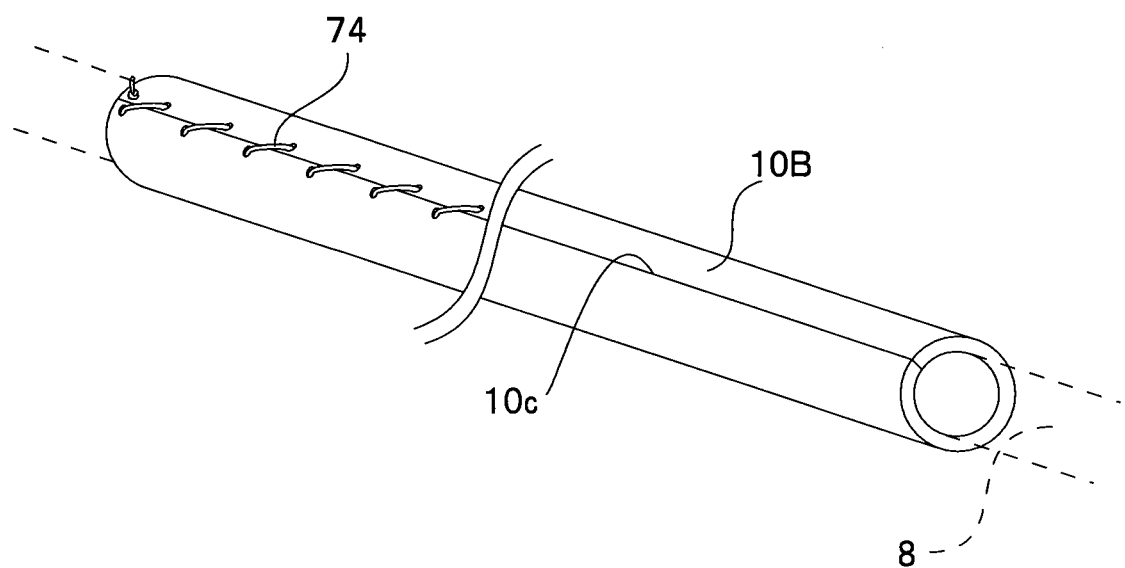
FIG. 26 is a view showing a state in which with the string-like member as the press mechanism for pressing and fixing the insertion portion of the endoscope inserted into the guide tube being tight, the inner peripheral surface of the guide tube presses the insertion portion according to the fourth embodiment.

FIG. 25 and FIG. 26 are cross-sectional views for explaining a press mechanism for pressing the insertion portion by the inner peripheral surface of the guide tube by decreasing an inner diameter of the entire guide tube using a string-like member. The press mechanism shown in FIG. 25 and FIG. 26 is composed of the string-like member through a plurality of holes provided along cut edges of the cylindrical guide tube cut along an axial direction.

FIG. 25 is a view showing a state in which with the string-like member as a press mechanism for pressing and fixing the insertion portion 8 of the endoscope inserted into the guide tube 10B being loose, the inner peripheral surface of the guide tube 10B does not press the insertion portion 8. FIG. 26 is a view showing a state in which with the string-like member as the press mechanism for pressing and fixing the insertion portion 8 of the endoscope inserted into the guide tube 10B being tight, the inner peripheral surface of the guide tube 10B presses the insertion portion 8. The guide tube 10B is a generally cylindrical member having a portion cut in one place parallel to the axial direction on a circumferential surface, that is, having a through-slit, and a plurality of holes 10d are provided near two cut opposed end surfaces 10c along the axial direction. In the state in FIG. 25, there is a predetermined space between the two end surfaces 10c. One string-like member 74 is provided to alternately pass the two end surfaces 10c and pass through the plurality of holes 10d. A knot 10e is formed at one end of the string-like member 74 so that one end of the string-like member 74 does not slip out of the holes 10d.

When the insertion portion 8 of the endoscope is inserted into the guide tube 10B, the guide tube 10B is in a state in which the string-like member 74 is loose, as shown in FIG. 25.

When the insertion portion 8 is fixed to the guide tube 10B, the other end of the string-like member 74 is pulled, so that the two end surfaces 10c are in proximity to or in close contact with each other, to press the insertion portion 8 by the inner peripheral surface of the guide tube 10B. One end of the string-like member 74 cannot pass through the holes 10d, and therefore, when the other end is pulled, the guide tube 10B is tightened, and the inner diameter of the guide tube 10B decreases, as shown in FIG. 26. As a result, the insertion portion 8 is fixed to the guide tube 10B.

When the insertion portion 8 of the endoscope is pulled out from the guide tube 10B, the guide tube 10B can be returned to the state in FIG. 25 by loosening the string-like member 74.

As described above, according to the guide tube in FIG. 25 and FIG. 26, the string-like member is tightened, and the inner peripheral surface of the guide tube 10B presses the outer peripheral portion of the insertion portion 8 of the endoscope, thereby, the insertion portion 8 is fixed to the guide tube 10B.

The plurality of holes 10d provided in the guide tube 10B may be provided over the entire end surfaces 10c of the guide tube 10B, or may be partly provided, distributed in a plurality of places.

Further, the string-like member also need not be passed through all the plurality of holes 10d. Also, using a plurality of the string-like members, rather than one string-like member, each may be distributed and passed through the holes 10d. A place tightened by the string-like member is preferably provided in the distal end portion of the guide tube 10B, and the portions where the vibration motor is located.

Figure 27:
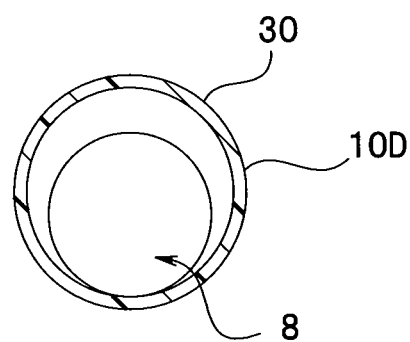
FIG. 27 is a cross-sectional view showing a state in which an inner diameter before heat is applied is larger than an outer diameter of the insertion portion according to the fourth embodiment.
Figure 28:
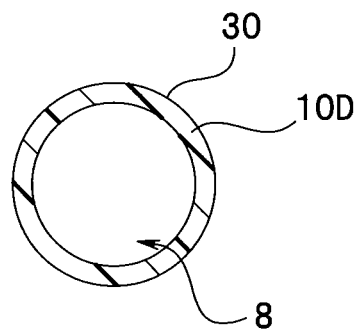
FIG. 28 is a cross-sectional view showing a state in which after heat is applied, a guide tube shrinks, the inner diameter of the guide tube decreases, and as a result, an inner peripheral portion of the guide tube presses an outer peripheral portion of the insertion portion, according to the fourth embodiment.

FIG. 27 and FIG. 28 are cross-sectional views for explaining a press mechanism for pressing the insertion portion by an inner peripheral surface of a guide tube by decreasing an inner diameter of the entire guide tube using heat shrinkage. A guide tube 10D is a heat-shrinkable cylindrical guide tube.

FIG. 27 is a cross-sectional view showing a state in which the inner diameter before heat is applied is larger than the outer diameter of the insertion portion 8. FIG. 28 is a cross-sectional view showing a state in which after heat is applied, the guide tube 10D shrinks, the inner diameter of the guide tube 10D decreases, and as a result, an inner peripheral portion of the guide tube 10D presses the outer peripheral portion of the insertion portion 8. In other words, the guide tube 10D itself shrinks by heat, and the shrinking guide tube itself brings the insertion portion into close contact with the inner peripheral surface. A place to be heat-shrunk is preferably provided in the distal end portion of the guide tube 10D, and portions where the vibration motor is located.

As described above, according to the guide tube in the present embodiment, the inner diameter of the guide tube can be decreased, using plastic deformation, the binding band, the string-like member, or heat shrinkability, to press the insertion portion to fix the insertion portion to the guide tube.

Fifth Embodiment

A guide tube in a fifth embodiment is a guide tube having a press mechanism for pressing an inner peripheral surface of the guide tube to the insertion portion by decreasing an inner diameter of the guide tube by suction action.

Figure 29:
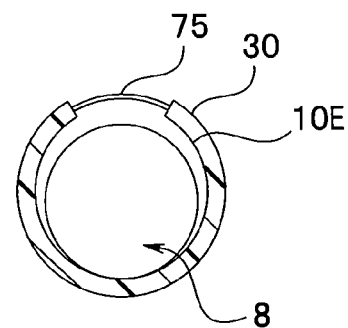
FIG. 29 is a view showing a state in which air enters a guide tube, and an inner peripheral surface of the guide tube does not press an insertion portion according to a fifth embodiment.
Figure 30:
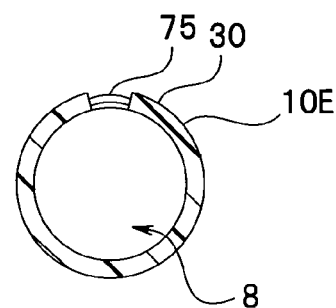
FIG. 30 is a view showing a state in which air is sucked from the guide tube, and the inner peripheral surface of the guide tube presses the insertion portion in close contact with the insertion portion according to the fifth embodiment.
Figure 31:
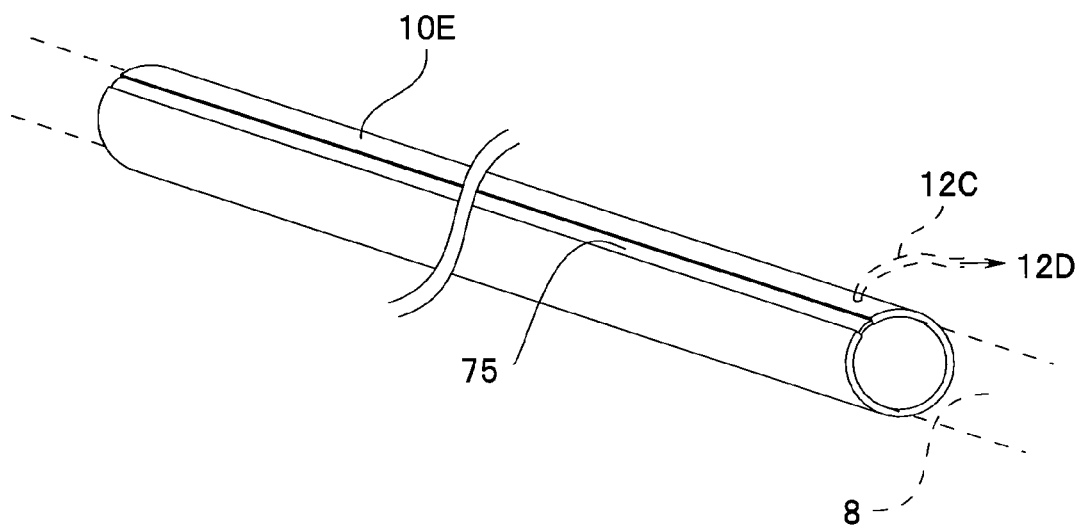
FIG. 31 is an appearance view of the guide tube in which interior air is sucked according to the fifth embodiment.

FIG. 29 to FIG. 31 are cross-sectional views for explaining a press mechanism for pressing the insertion portion by an inner peripheral surface of a guide tube by sucking air in the guide tube to decrease an inner diameter of the entire guide tube. A press mechanism of a guide tube 10E is constituted by including a stretchable film member provided along a cut through-slit of the generally cylindrical guide tube cut along an axial direction to have the through-slit.

FIG. 29 is a view showing a state in which air enters the guide tube 10E, and the inner peripheral surface of the guide tube 10E does not press the insertion portion 8. FIG. 30 is a view showing a state in which air is sucked from the guide tube 10E, and the inner peripheral surface of the guide tube 10E presses the insertion portion 8 in close contact with the insertion portion 8. FIG. 31 is an appearance view of the guide tube 10E in which interior air is sucked. The guide tube 10E is a cylindrical member having a portion cut along axial direction, that is, a through-slit, and a stretchable film member 75 is provided between the two cut opposed end surfaces. The film member 75 is a fluororubber, a silicone rubber having a surface coated with fluorine, or the like. Also, although not shown, the tightening mechanism described in FIG. 8 and FIG. 9 is provided at a distal end portion and a proximal end portion of the guide tube, so that an interior of the guide tube 10E can be kept in an enclosed state by the tightening mechanisms shown in FIG. 8 and FIG. 9, and the film member 75.

When the insertion portion 8 of the endoscope is inserted into the guide tube 10E, air is present in the interior of the guide tube 10E, and the inner diameter of the guide tube 10E is larger than the outer diameter of the insertion portion 8, as shown in FIG. 29.

Also, when the insertion portion 8 is fixed to the guide tube 10E after insertion of the insertion portion 8 into the guide tube 10E is finished, the cylinder 52 of the tightening mechanism shown in FIG. 8 and FIG. 9 is rotated to press the cylinder 51 to put the interior of the guide tube 10E in an enclosed space. With an interior space of the guide tube 10E enclosed, interior air is sucked from an end of the guide tube 10E by an electric pump or the like to put the guide tube 10E in a state as in FIG. 30.

A configuration for sucking air in the guide tube 10E or supplying air into the guide tube 10E can be implemented by using the electric pump 12D, the press control portion 12E, and the like as described in the first embodiment. Interior air is sucked by the electric pump 12D via the duct 12C.

As described above, according to the guide tube in the present embodiment, by sucking air in the guide tube, the inner diameter of the guide tube can be decreased to fix the insertion portion to the guide tube.

Therefore, the guide tube according to each embodiment described above is constituted separately from the endoscope, and during vibration of the guide tube, the guide tube presses the insertion portion of the endoscope to integrate the insertion portion of the endoscope and the guide tube. As a result, in the guide tube into which the insertion portion of the endoscope and the like are inserted, a reduction in an exciting force on the cilia can be suppressed.

Particularly, the guide tube and the endoscope are separate, and therefore, even if the press mechanism of the guide tube breaks down and so on, only the guide tube is replaced, and the endoscope apparatus can be used as it is, which is also economical.

Therefore, according to each embodiment, it is possible to implement a guide tube into which an insertion portion of an endoscope and the like are inserted, wherein a reduction in an exciting force on cilia can be suppressed, a guide tube apparatus having the guide tube, an endoscope system having the guide tube, and a method for self-propelling a guide tube.

The present invention is not limited to the above-described embodiments and modifications, and various changes and alterations can be made without departing from the gist of the present invention.

What is claimed is:

1. A guide tube comprising:
a tube;
a ciliary portion composed of many cilia inclined in a longitudinal direction of the tube, provided in an outer peripheral portion of the tube; and
a press mechanism configured for pressing a member inserted inside the tube,
wherein the press mechanism has a press member provided in the tube configured for pressing the inserted member, and
wherein the press member is a screw, and
the screw is provided in the tube so as to threadingly engage a screw hole provided in a tube wall portion of the tube and press an insertion portion of an endoscope inserted inside the tube.

2. A guide tube comprising:
a tube;
a ciliary portion provided on an outer peripheral surface of the tube and composed of many cilia inclined in a longitudinal direction of the tube; and
a spring member configured for pressing an insertion portion of an endoscope inserted inside the tube,
wherein the tube has an opening portion on a wall surface thereof,
one end of the spring member is fixed to a periphery of the opening portion of the tube and an other end of the spring member is located at the opening portion as a movable end, and
the movable end of the spring member located at the opening portion is pressed and engaged between an inner wall surface of the tube and the insertion portion of the endoscope and thereby the insertion portion is pressed by an elastic force of the spring member to be fixed to the tube.

3. A guide tube comprising:
a tube;
a ciliary portion composed of many cilia inclined in a longitudinal direction of the tube, provided in an outer peripheral portion of the tube; and
a press mechanism configured for pressing a member inserted inside the tube, wherein the press mechanism has a press member provided in the tube configured for pressing inserted member, and
wherein the press member is a rotating member, and
the rotating member is provided to the tube so that the rotating member is rotatable with respect to a tube wall portion of the tube and one end of the rotating member presses an insertion portion of an endoscope inserted inside the tube, by rotation.

4. A guide tube comprising:
a tube;
a ciliary portion provided on an outer peripheral surface of the tube and composed of many cilia inclined in a longitudinal direction of the tube; and
a press mechanism configured for pressing an insertion portion of an endoscope inserted inside the tube,
wherein the press mechanism has a first cylinder provided at a distal end of the tube, and a second cylinder which is threadingly engaged with the first cylinder and configured to press the first cylinder towards the insertion portion, and
wherein the first cylinder is made of a resin and has a screw thread on an outer peripheral surface thereof,
the second cylinder has a threaded portion which is provided on an inner peripheral surface of the second cylinder and has a screw thread capable of threadingly engaging with the screw thread of the first cylinder, and a taper portion, having an inner diameter of the second cylinder, gradually decreases toward a distal end side, and
the second cylinder is threadingly engaged with the first cylinder, and thereby the taper portion of the second cylinder presses an outer peripheral surface of the first cylinder on a distal end side thereof and a distal end portion of the pressed first cylinder deforms toward the insertion portion, so that the deformed distal end portion presses the insertion portion to be fixed to the tube.

5. A guide tube comprising:
a tube;
a ciliary portion composed of many cilia inclined in a longitudinal direction of the tube, provided in an outer peripheral portion of the tube; and
a press mechanism configured for pressing a member inserted inside the tube, and
wherein the press mechanism has the tube that is heat-shrinkable.

6. A guide tube comprising:
a tube;
a ciliary portion composed of many cilia inclined in a longitudinal direction of the tube, provided in an outer peripheral portion of the tube; and
a press mechanism configured for pressing a member inserted inside the tube, and
wherein the press mechanism is a mechanism for tightening the tube with a string-like member.

* * * * *